United States Patent [19]
Hawkins

[11] Patent Number: 5,730,628
[45] Date of Patent: Mar. 24, 1998

[54] MULTI-CONTACT CONNECTOR FOR AN IMPLANTABLE MEDICAL DEVICE

[75] Inventor: Rodney J. Hawkins, Culver City, Calif.

[73] Assignee: Pacesetter, Inc., Sylmar, Calif.

[21] Appl. No.: 719,932

[22] Filed: Sep. 25, 1996

[51] Int. Cl.⁶ ............................................. H01R 13/187
[52] U.S. Cl. ........................... 439/843; 439/909; 607/37
[58] Field of Search ................................. 439/843, 909, 439/851, 846, 856, 857, 675; 607/37, 116

[56] References Cited

U.S. PATENT DOCUMENTS

| | | | |
|---|---|---|---|
| 2,549,577 | 4/1951 | Coyle | 173/269 |
| 3,161,451 | 12/1964 | Neidecker | 439/843 |
| 3,381,262 | 4/1968 | Jeanrenaud | 339/258 |
| 3,760,332 | 9/1973 | Berkovits et al. | 339/66 R |
| 4,002,400 | 1/1977 | Evans | 339/258 R |
| 4,112,953 | 9/1978 | Shanker et al. | 439/843 |
| 4,120,557 | 10/1978 | Horrocks | 439/843 |
| 4,572,606 | 2/1986 | Neumann et al. | 339/262 R |
| 4,764,132 | 8/1988 | Stutz, Jr. | 439/810 |
| 4,898,173 | 2/1990 | Daglow et al. | 128/419 P |
| 5,069,209 | 12/1991 | Posin | 128/419 P |
| 5,070,605 | 12/1991 | Daglow et al. | 29/842 |
| 5,088,942 | 2/1992 | Welsh et al. | 439/843 |

FOREIGN PATENT DOCUMENTS

| | | | |
|---|---|---|---|
| 0569369 | 11/1975 | Switzerland | 439/851 |

Primary Examiner—Gary F. Paumen
Assistant Examiner—Tho Dac Ta

[57] ABSTRACT

An electrical connector assembly is provided for detachably coupling an electrical lead to a medical device. A hollow barrel has a through passage which extends between proximal and distal ends. A leaf spring member includes a base element on the barrel adjacent the distal end and a plurality of integral resilient spring elements extend away from the distal end at a plurality of circumferentially spaced locations to tip ends adjacent the proximal end. The leaf spring elements have contact portions intermediate the base element and the tip ends projecting and biased toward a longitudinal axis of the barrel for mating engagement with a proximal end of the electrical lead when inserted into the barrel from the distal end. A guide device on the barrel adjacent the proximal end and overlying the tip ends of the resilient spring elements serves to guide the electrical lead past the tip ends of the resilient spring elements without engaging the tip ends both during insertion and extraction. The passage through the hollow barrel preferably includes a first cylindrical passage defined by a first diameter and extends away from the distal end and a second cylindrical passage defined by a second diameter greater than the first diameter extends away from the proximal end. The second cylindrical passage is a stop surface for terminal engagement by the resilient spring elements when so moved by the electrical lead as it is inserted from the distal end of the barrel.

2 Claims, 3 Drawing Sheets

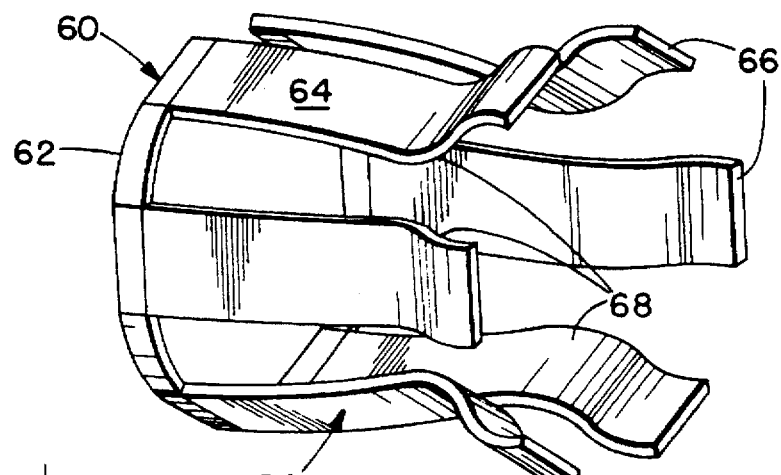
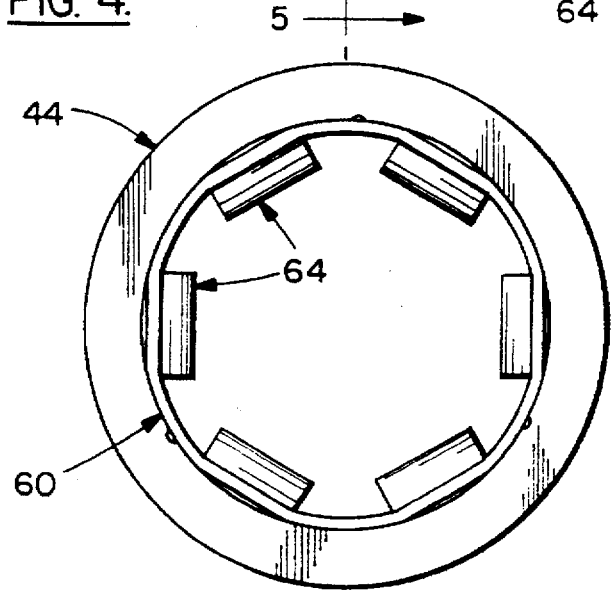
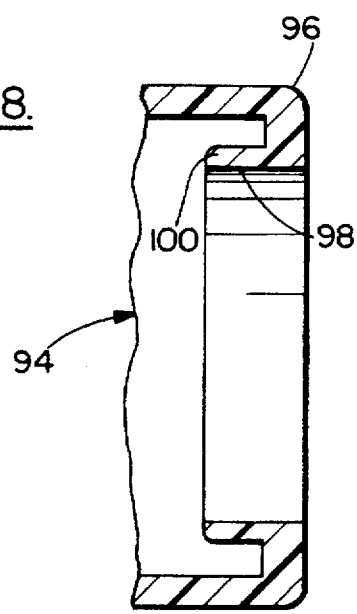
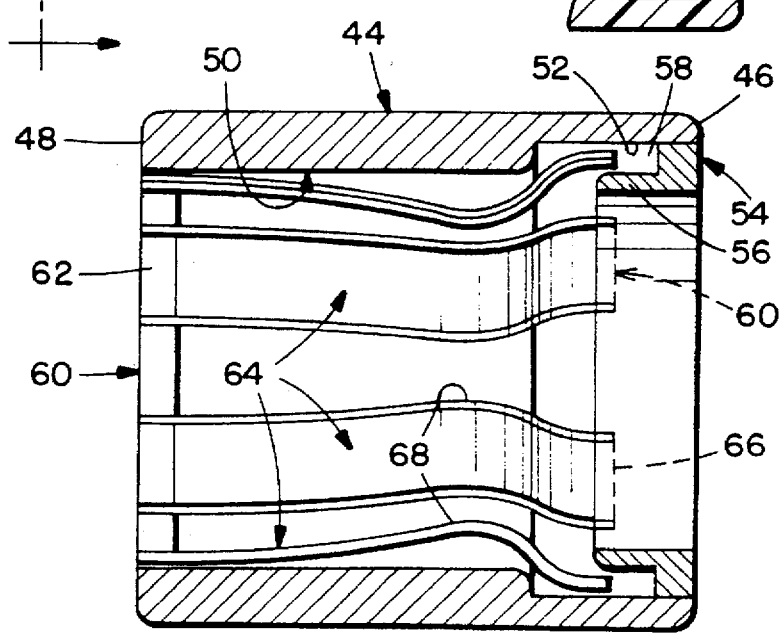

MULTI-CONTACT CONNECTOR FOR AN IMPLANTABLE MEDICAL DEVICE

FIELD OF THE INVENTION

This invention relates generally to an electrical connector assembly for detachably coupling an electrical lead to a medical device and, more particularly, to an improved spring contact design which assures optimal electrical contact while requiring minimal insertion and extraction forces and limiting spring deflection so as to avoid exceeding the yield stress limit.

BACKGROUND OF THE INVENTION

The invention will be described herein in connection with its use as a pacemaker terminal for connecting and releasing by hand pressure the proximal end of an electrode lead to an implantable heart pacemaker. However, it will be apparent to those skilled in the art that the invention has broader applicability to electrical terminals generally, irrespective of the device to which the lead is to be connected.

The operation of an implantable heart pacemaker requires the transmission of low level electrical signals, generated by the heart to the pacemaker, as well as the pacing voltages generated by the pacemaker to the heart. This physical link of transmission, the pacemaker lead, is a section of high-fatigue-resistant, multi-insulated electrical conductor designed to endure the severe environment inside the human body. Any leakage of body fluids or passage of body ions into the conductor can result in a deterioration of the signals transmitted. The distal end of the lead, in the form of an electrode, provides the fixation to the heart tissue. The proximal end of the lead, in the form of a pin, is connected to the terminal of the pacemaker. The materials used to construct the pacemaker lead must be biocompatible. For insulation, common selections are silicone rubber, epoxy, or polyurethane. For the conductors, common selections are titanium and its alloys, 316L stainless steel and its derivatives, or platinum and its alloys.

To transmit these electrical signals from the implantable medical device, such as a pacemaker or a cardiac defibrillator, to the heart, implantable leads are used which make electrical contact with the device through the connector top ring and tip contacts. The signals are then transmitted from the device to the heart via the implantable leads.

The common way of making electrical contact between the lead and the device is by the use of a mechanical spring within the connector lead bore. These springs have to maintain a minimum contact force to ensure a good electrical path. After several insertions and extractions of the lead from the device or the use of an over-sized lead, these mechanical springs tend to loosen up and decrease their contact force. This problem occurs when the maximum spring deflection is exceeded. Once the spring is over stressed by exceeding its yield point, the spring will deform permanently.

Hence, the goals sought for a connector used in such an environment include the following:

to provide a spring contact mechanism that limits the spring deflection thus avoiding exceeding the yield stress limit;

to provide a spring contact mechanism that has low insertion and extraction forces; and to provide a spring contact which has a plurality of contact points, that is, redundancy of connections to assure a good electrical path between the lead and the device.

It was in light of the foregoing that the present invention was conceived and is now hereby reduced to practice.

SUMMARY OF THE INVENTION

An electrical connector assembly is provided for detachably coupling an electrical lead to a medical device. A hollow barrel has a through passage which extends between proximal and distal ends. A leaf spring member includes a base element on the barrel adjacent the distal end and a plurality of integral resilient spring elements extend away from the distal end at a plurality of circumferentially spaced locations to tip ends adjacent the proximal end. The leaf spring elements have contact portions intermediate the base element and the tip ends projecting and biased toward a longitudinal axis of the barrel for mating engagement with a proximal end of the electrical lead when inserted into the barrel from the distal end. A guide device on the barrel adjacent the proximal end and overlying the tip ends of the resilient spring elements serves to guide the electrical lead past the tip ends of the resilient spring elements without engaging the tip ends both during insertion and extraction. The passage through the hollow barrel preferably includes a first cylindrical passage defined by a first diameter and extends away from the distal end and a second cylindrical passage defined by a second diameter greater than the first diameter extends away from the proximal end. The first cylindrical passage is a stop surface for terminal engagement by the resilient spring elements when so moved by the electrical lead as it is inserted from the distal end of the barrel.

The invention thus comprises three distinct parts:

(a) a leaf spring member of simple cantilever construction;

(b) a barrel or housing; and (c) an end plug.

The leaf spring member is preferably formed from a single piece, for example, a flat sheet of MP35N alloy although other materials may be used. The flat sheet is then bent with the desired radii and rolled into a cylinder. The leaf spring member is then inserted into an end of the barrel and is spot welded or laser welded to one end of the barrel. Once the leaf spring member is in place, the plug is then attached to the other end of the barrel as by press fit or welding. The plug secures the other end of the barrel and provides a clearance area for the spring to deflect when it is compressed. It also prevents the seals of the lead from getting caught on the ends of the leaf spring member when the lead is removed.

Without the implantable leads in place, the leaf spring is mechanically undisturbed. Once the lead is inserted, the spring will deflect until it clears all diameters of the lead. If the seal diameters of the lead are too large or their material is too rigid, the smallest inner diameter of the barrel will act as a limit stop thereby avoiding over-stressing of the spring.

The leaf spring member provides a plurality of contact points, for example, six contact points. These contact points may be six equally spaced flats or spring elements equally spaced around the spring member. These six flats or spring elements provide sufficient contact force to maintain a good electrical path between the lead and the device. In addition, these flats deflect very easily because they are only attached at one end, modeling a simple cantilever beam. This simple cantilever design concept provides for the low minimal insertion and extraction force required.

Other advantages of the invention include its interchangeability with other known designs, the minimal tooling required for the fabrication and assembly of the invention, and the ease of installation of the connector of the invention into a receiving medical device.

A design variation for the electrical connector assembly of the invention exists for the barrel part. The barrel may be constructed of two concentric metal tubes with different diameters. The smaller diameter tube is press fitted into the larger diameter tube providing the spring deflection limit stop. Both tubes would be flush at one end in order to provide for the clearance area over the plug. The leaf spring member is then spot or laser welded onto the smaller diameter tube. This design variation would require an additional part to the assembly. The barrel would not be required to be machined but rather would be formed out of extruded metal tubing. While extruding a tube may be less expensive than machining that part, however, it must be recognized that the added assembly time may offset the savings achieved such that this design variation may not actually offer a saving over the machined unit.

Accordingly, a primary object of the present invention is to provide an improved terminal for providing an effortless, positive and secure mechanical and electrical connection of an electrical lead to an electrical device, for example, an implantable heart pacemaker.

A further object of the invention is an improved terminal for providing effortless, simple and reliable disconnection of the electrical lead from the electrical device, when required.

Another object of the invention is an improved pacemaker terminal which eliminates the need for the use of any special tools, including a set screw, or connecting and disconnecting the proximal end of an electrode lead to a pacemaker terminal.

Still another object of the present invention is to provide an electrical connector assembly for detachably coupling an electrical lead to a medical device and, more particularly., to an improved spring contact design which assures optimal electrical contact while requiring minimal insertion and extraction forces and limiting spring deflection so as to avoid exceeding the yield stress limit.

Still a further object of the present invention is to provide such an electrical connector assembly for detachably coupling an electrical lead to a medical device which comprises a hollow barrel extending between proximal and distal ends and having a passage therethrough, a leaf spring member including a base element integral with said barrel adjacent said distal end thereof and a plurality of integral resilient spring elements extending away from the distal end at a plurality of circumferentially spaced locations to tip ends adjacent the proximal end, the leaf spring elements having contact portions intermediate the base element and the tip ends projecting and biased toward the longitudinal axis of the barrel for mating engagement with a proximal end of the electrical lead when inserted into the barrel from the distal end and generally aligned with the longitudinal axis, and guide members on the barrel adjacent the proximal end and overlying the tip ends of the resilient spring elements for guiding the electrical lead past the tip ends of the resilient spring elements without engaging the tip ends.

Yet a further object of the present invention is to provide such an electrical connector assembly in which the passage through the hollow barrel includes a first cylindrical passage defined by a first diameter and extending away from the distal end and a second cylindrical passage defined by a second diameter greater than the first diameter and extending away from the proximal end, the second cylindrical passage being a stop surface for terminal engagement by the resilient spring elements when so moved by the electrical lead as it is inserted from the distal end of the barrel.

Still another object of the invention is to provide such an electrical connector assembly wherein the resilient spring elements are equally spaced circumferentially.

Yet another object of the invention is to provide such an electrical connector assembly wherein the guide means includes a circular plug integral with the barrel adjacent the proximal end, the plug having an annular flange spaced from the inner cylindrical surface extending toward the distal end of the barrel and, together with the inner cylindrical surface, defining an annular recess for freely receiving the tip ends, the annular flange guiding the electrical lead past the tip ends of the resilient spring elements without engaging the tip ends.

Yet a further object of the invention is to provide such an electrical connector assembly wherein the barrel, the plug, and the leaf spring member are of one piece electrically conductive construction.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 3 is a detail perspective view of one component of the electrical connector assembly of the invention, namely, the leaf spring member;

FIG. 4 is an end elevation view of the electrical connector assembly of the invention viewed from the distal end thereof;

FIG. 5 is a cross-section view taken generally along line 5—5 in FIG. 4;

FIG. 8 is a detail cross-section view illustrating yet another embodiment of the electrical connector assembly of the invention.

DETAILED DESCRIPTION OF THE PREFERRED EMBODIMENT

Figure 1:
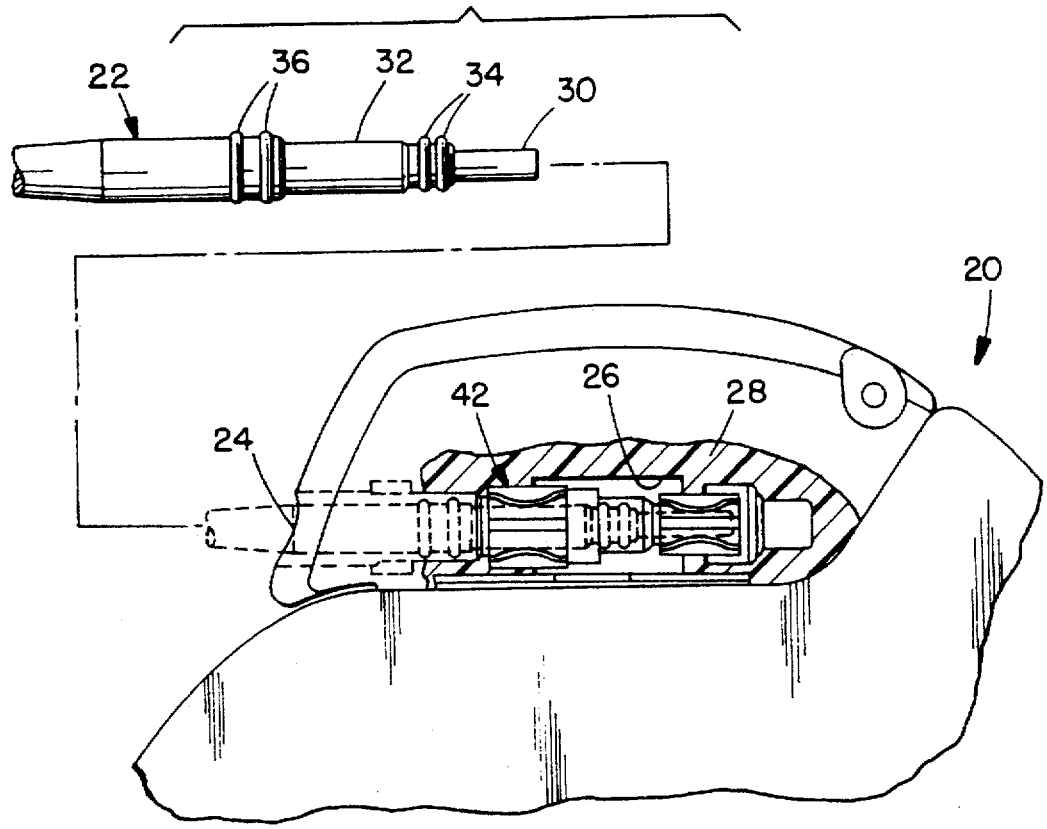
FIG. 1 is a detail exploded side elevation view, partly cut away and shown in section, of an exemplary medical device, specifically a pacemaker, and an associated electrical lead to be coupled to the pacemaker, the pacemaker being modified to embody the electrical connector assembly of the invention.

Turn now to the drawings and, initially, to FIG. 1 which is a detail side elevation view, partial cutaway, of a medical device 20 such as a pacemaker and an associated electrical lead 22 intended to be inserted through an opening 24 into a receiving cavity or lumen 26 of a conductor block 28 integral with the medical device. The electrical lead 22 is depicted by dashed lines within the pacemaker as it would be positioned when fully inserted into the conductor block 28. The electrical lead 22 is illustrated as being of a bipolar construction having first and second cylindrical poles or contacts 30, 32 and also has a plurality of longitudinally spaced sealing rings 34, 36 which seal the lumen 26 against fluid entry and provide a seal intermediate the contacts 30, 32.

Figure 2:
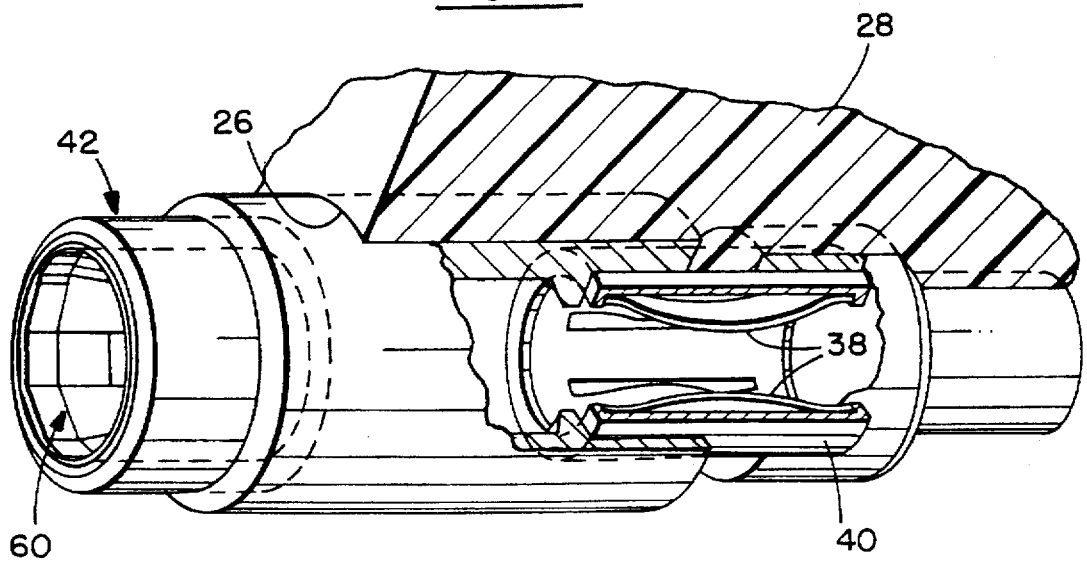
FIG. 2 is a detail perspective view of components illustrated in FIG. 1 and including the electrical connector assembly of the invention.

The receiving lumen 26 is stepped with the proximal end (to the right, viewing FIG. 1) being of reduced diameter to receive the first contact 30 in the form of a pin. A spring member 38 held in a suitable retainer 40 is engaged by the first contact 30 to make electrical coupling when the electrical lead is fully inserted. An electrical connector assembly 42 (FIGS. 1 and 2) embodying the invention is located within the lumen 26 and distally of the spring member 38 and retainer 40 for making electrical coupling with the second contact 32 in a manner to be described.

Turning to FIGS. 3, 4, and 5, the electrical connector assembly 42 comprises a hollow barrel 44 which extends between proximal and distal ends 46, 48, respectively. The barrel 44 has a first cylindrical passage 50 defined by a first diameter and extending away from the distal end 48 and a second cylindrical passage 52 defined by a second diameter and extending away from the proximal end 46. A circular plug 54 is fixed to the second cylindrical passage adjacent the proximal end, as by interference fit, welding, or the like, and the plug has an annular flange 56 spaced from the barrel and extending toward the distal end of the barrel and, together with the barrel, defining an annular recess 58. A leaf spring member 60 includes a base element 62 fixed to the first cylindrical passage adjacent the distal end 48 of the barrel 44 and a plurality of integral resilient spring elements 64 extending from the base element at a plurality of circumferentially spaced locations to tip ends 66 freely received in the annular recess 58 for limited transverse movement between the second cylindrical passage 52 and the annular flange 56. The leaf spring elements 64 have contact portions 68 intermediate the base element 62 and the tip ends 66 which project and are biased toward the longitudinal axis of the barrel for mating engagement with a proximal end of the electrical lead 22, specifically with the second contact 32 when inserted into the barrel from the distal end 48 and generally aligned with the longitudinal axis of the barrel. Preferably, the resilient spring elements 64 extend from the base element 62 at a plurality of equally spaced circumferential locations to maximize uniformity of contact force between the spring elements and the second contact 32 of the electrical lead 22.

Figure 6:
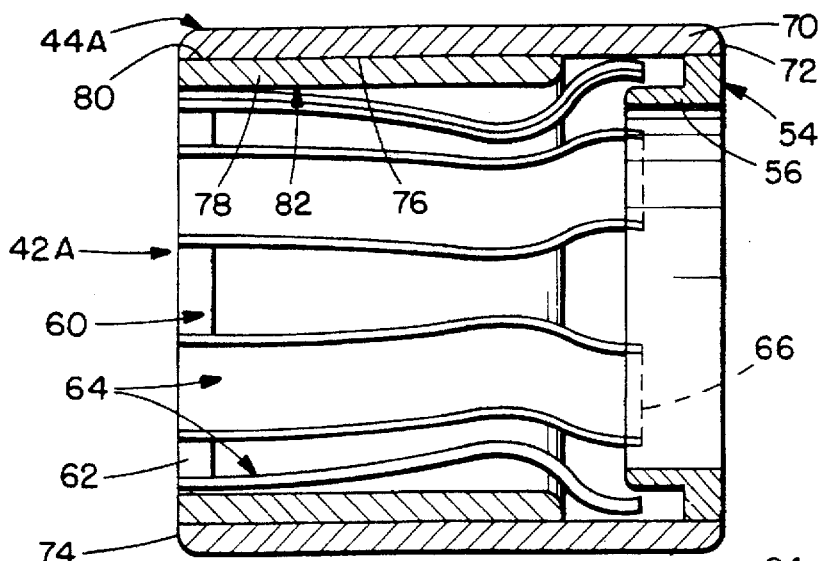
FIG. 6 is a cross-section view, similar to FIG. 5 but illustrating another embodiment of the electrical connector assembly of the invention.

In another embodiment illustrated in FIG. 6, a modified electrical connector assembly 42A includes a modified barrel 44A comprised of an outer sleeve 70 which extends between proximal and distal ends 72, 74 and has an inner cylindrical surface 76. An inner sleeve 78 has an outer cylindrical peripheral surface 80 which is fittingly engaged with the inner cylindrical surface 76 of the outer sleeve 70 and extends from a distal end generally proximate the distal end of the outer sleeve to locations intermediate the proximal and distal ends 72, 74, respectively, of the modified barrel. The inner sleeve also has a first cylindrical passage 82 therethrough which is generally equivalent to the passage 50 of the electrical connector assembly 42.

Whereas the barrel 44 would likely be formed by machining, the barrel 44A would likely be formed by joining the sleeves 70, 78 by force-fitting, welding, or using any other suitable technique. In this embodiment, the leaf spring member 60 and the circular plug 54 would be the same as in the earlier described embodiment.

In the barrel 44, the first cylindrical passage 50 is defined by a first diameter and the second cylindrical passage 52 is defined by a second diameter greater than the first diameter. In the barrel 44A, the first cylindrical passage 82 is similarly defined by a first diameter and the inner cylindrical surface 76, generally equivalent to the second cylindrical passage 52 of barrel 44, is defined by a second diameter greater than the first diameter. In each instance, the second cylindrical passage is a stop surface for terminal engagement by the resilient spring elements 64 when they are so moved by the electrical lead 22 as it is inserted from the distal end of the barrel. With this construction, the movement of the spring elements 64 is restricted to assure that they do not exceed their elastic limit, preventing fatigue and thereby substantially increasing the lifetime of the connector for the medical device 20.

In each of the embodiments just disclosed and, indeed, in all of the subsequent embodiments to be disclosed, the circular plug 54 with its annular flange, and equivalent constructions to be described, serves as a guide member on the barrel adjacent the proximal end and overlying the tip ends 66 of the resilient spring elements 64 for guiding in a free and unobstructed fashion the electrical lead 22, and especially the sealing rings 34, past the tip ends of the resilient spring elements without engaging the tip ends. If the electrical lead were so to engage the tip ends 66, damage to the lead and to the connector assembly could result. The plug 54 further operates to prevent the tip ends 66 from projecting beyond the proximal end of the barrel.

Figure 7:
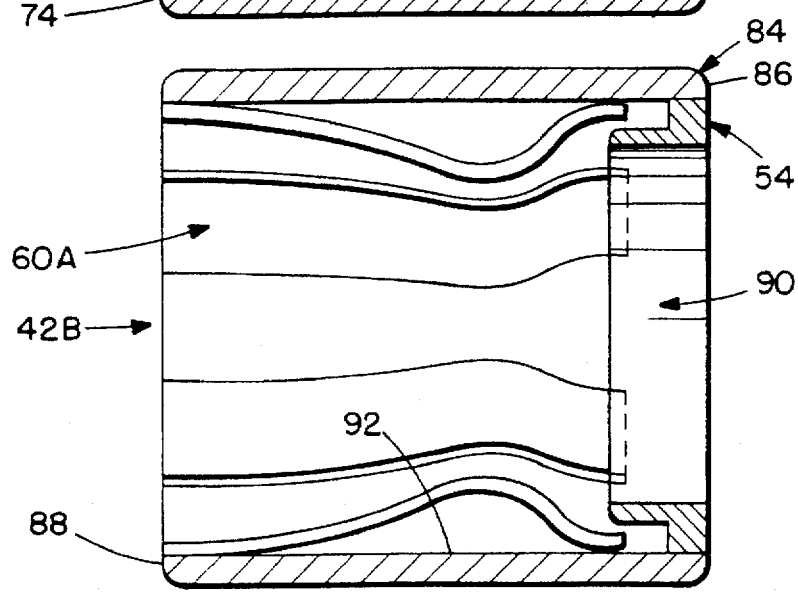
FIG. 7 is a cross-section view, similar to FIG. 5 but illustrating still another embodiment of the electrical connector assembly of the invention.

Turn now to FIG. 7 for the description of another embodiment of the invention, a modified electrical connector assembly 42B. In this instance, a hollow barrel alone extends between proximal and distal ends 86, 88, respectively, and has a passage 90 therethrough defined by an inner cylindrical surface 92. A leaf spring member 60A is in all respects like the leaf spring member 60 except that it must operate in an assembly in which the diameter of the inner cylindrical surface 92 is constant between the proximal and distal ends 86, 88. Also, the circular plug 54 is unchanged from the earlier embodiments. While the constructions of the barrels 44 and 44A are preferred to that of the barrel 84, the latter is adequate for purposes of the invention.

In FIG. 8, another modified construction is illustrated in which a hollow barrel 94 has, at its proximal end 96, an integral guide member 98 with a distally extending annular flange 100 which together operate in an equivalent manner to the circular plug of the earlier described embodiments.

Figure 9:
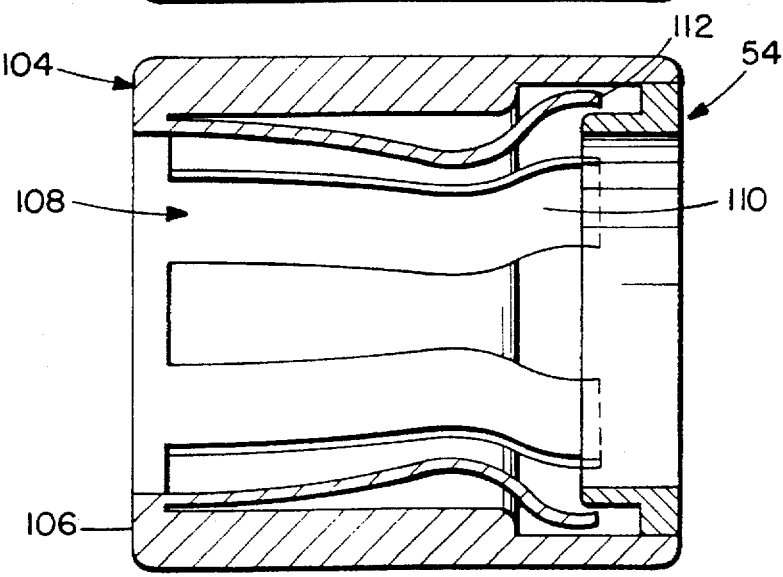
FIG. 9 is a cross-section view, similar to FIG. 5 but illustrating yet a further embodiment of the electrical connector assembly of the invention.

In FIG. 9, yet another modified construction is illustrated in which a hollow barrel 104 has, at its distal end 106, an integral leaf spring member 108 similar in construction and operation to the leaf spring members 60 and 60A, including a plurality of proximally extending spring elements 110 with tip ends 112 protected by the circular plug 54 of the earlier described embodiments.

It will also be understood as being within the purview of the invention to fabricate a further modified electrical connector assembly as a combination of the constructions illustrated in FIGS. 8 and 9 such that the barrel, the plug, and the leaf spring member are of one piece electrically conductive construction.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An electrical connector assembly for detachably coupling an electrical lead to a medical device comprising:

a hollow barrel having a longitudinal axis and extending between proximal and distal ends and having a first cylindrical passage defined by a first diameter and extending away from said distal end and a second cylindrical passage defined by a second diameter and extending away from said proximal end;

a circular plug fixed to said second cylindrical passage adjacent said proximal end, said plug having an annular flange spaced from said barrel extending toward the distal end of said barrel and, together with said barrel, defining an annular recess; and a leaf spring member including a base element fixed to said first cylindrical passage adjacent said distal end of said barrel and a plurality of integral resilient spring elements extending therefrom in a cantilevered manner at a plurality of circumferentially spaced locations to tip ends freely received in the annular recess for limited transverse movement between said second cylindrical passage and said annular flange, said sprang elements being uniformly spaced from said first cylindrical passage and from said second cylindrical passage along the entire length of said leaf spring member beyond said base element, said spring elements having contact portions intermediate said base element and said tip ends, said contact portions being nearer the longitudinal axis of said barrel than other portions thereof, said contact portions projecting and biased toward the longitudinal axis of said barrel for mating engagement with a proximal end of the electrical lead when inserted into said barrel from said distal end and generally aligned with the longitudinal axis thereof, said tap ends being moved into terminal engagement with said second cylindrical passage upon mating engagement of said contact portions by the electrical lead;

whereby movement of said spring elements is restricted to assure that they do not exceed their elastic limit.

2. An electrical connector assembly, as set forth in claim 1, wherein said resilient spring elements are equally spaced circumferentially.

* * * * *